United States Patent [19]

Chao

[11] Patent Number: 4,792,629

[45] Date of Patent: Dec. 20, 1988

[54] ALKYLATION OF AMINE COMPOUNDS

[75] Inventor: Kuo-Hua Chao, Houston, Tex.

[73] Assignee: Shell Oil Company, Houston, Tex.

[21] Appl. No.: 17,501

[22] Filed: Feb. 24, 1987

[51] Int. Cl.$^4$ ............................................. C07C 85/00
[52] U.S. Cl. .................................. 564/463; 564/467; 564/469; 564/470
[58] Field of Search ............... 564/463, 467, 469, 470; 502/152

[56] References Cited

U.S. PATENT DOCUMENTS 4,361,497 11/1982 Boldt et al. ........................ 502/152
4,430,513 2/1984 Homeier ............................ 564/467
4,448,996 5/1984 Yanagi et al. ..................... 564/467
4,562,291 12/1985 Wilson, Jr. et al. ............... 564/463

Primary Examiner—Glennon H. Hollrah
Assistant Examiner—John A. Sopp

[57] ABSTRACT

Alkylamines are self-alkylated to longer carbon chain alkylamines using a catalyst mixture comprising ruthenium carbonyl and a compound of the formula (cyclopentadienyl)$_n$MY$_{4-n}$ where M is Zr, Hf or Ti, Y is individually selected from hydrogen, $C_1$-$C_5$ alky, $C_6$-$C_{20}$ aryl, $C_1$-$C_{25}$ metalalkyl and halogen and n is 1, 2, 3 or 4.

17 Claims, No Drawings

ALKYLATION OF AMINE COMPOUNDS

FIELD OF THE INVENTION

The present invention relates to the catalytic synthesis of longer chain alkylamines by the oligomerization or self-alkylation of mono-, di- and trialkylamines.

BACKGROUND OF THE INVENTION

The common method of alkylating organic compounds is by using alkylating agents such as olefins or alkylhalides in the presence of a Friedel Crafts catalyst. When amines are used as alkylating agents with Friedel Crafts catalysts, the alkylation reaction is severely inhibited by the fact that the amine poisons the catalyst by the formation of an acid-base compound.

U.S. Pat. No. 4,430,513, issued Feb. 7, 1984, discloses one method in which alkylamines can satisfactorily be used as alkylating agents. Specifically, this patent teaches the self-alkylation of alkylamine compounds which contain at least two alkyl substituents containing from about 2 to 6 carbon atoms. The alkylamine compounds are alkylated in the presence of a rhodium or cobalt carbonyl or a rhodium or cobalt compound which is capable of forming a carbonyl under alkylation conditions.

U.S. Pat. No. 4,562,291, issued Dec. 31, 1985, discloses the self-alkylation of mono-, di- and trialkylamines using a catalyst mixture comprising a tetrafluoroborate salt and a ruthenium, an osmium or an iridium-containing compound.

In co-pending U.S. application Ser. No. 940,385 filed Dec. 10, 1986, is discussed the use of a catalyst mixture comprising aluminum chloride in combination with cobalt and/or ruthenium carbonyl.

The oligomerized alkylamines prepared by the process of the instant invention are useful for preparing detergent products and disinfectant products.

SUMMARY OF THE INVENTION

The present invention involves a process for the catalytic synthesis of long chain alkylamines. Specifically, mono-, di- or trialkylamines are oligomerized or self-alkylated to form longer chain alkylamines by contacting the mono-, di- and/or trialkylamines with a catalyst mixture comprising a first component selected from a ruthenium carbonyl, a ruthenium-containing compound capable of being converted to a carbonyl under oligomerization conditions and mixtures thereof and a second component having the general formula (cylopentadienyl)$_n$MY$_{4-n}$ where M is zirconium, hafnium or titanium, Y is individually selected from the group consisting of hydrogen, $C_1$–$C_5$ alkyl, $C_6$–$C_{20}$ aryl, $C_1$–$C_{25}$ metalloalkyl and halogen and n is an integer ranging from 1 to 4. The mole ratio of ruthenium carbonyl or compound to zirconium, hafnium and/or titanium ranges from about 100:1 to about 1:100. Preferably this mole ratio will be about 1:1. A particular advantage of the instant invention is that it can be used to convert alkylamines to their mono-alkylated amine products in high yield. Selectivities of the instant catayst combinations result in the product amines being predominantly (i.e., a major proportion) the mono-alkylates. This can result in simpler product mixes with concomitant lower separation costs.

DETAILED DESCRIPTION OF THE INVENTION

The present invention provides a process for synthesizing long chain alkylamines by self-alkylation or oligomerization of shorter chain alkylamines. Any typical alkylamine can be oligomerized in accordance with the present invention. The invention is particularly suitable for alkylating trialkylamines, particularly the $C_1$–$C_6$ alkyl amines. Oligomerization produces a mixture of various longer chain alkylamines. In a preferred embodiment, the instant process converts an amine predominately to its next higher alkylated homologues i.e., the mono-alkylated amines. For example, triethylamine is converted predominately to butyldiethylamine with significant amounts of butylethylamine being also produced. Thus, in a preferred embodiment amines of the general formula

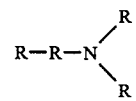

are prepared from amines of the general formula

wherein R is alkyl, preferably $C_1$–$C_6$ alkyl.

The reaction is run in the presence of a catalyst mixture comprising a first component selected from a ruthenium carbonyl, a ruthenium-containing compound cable of being converted to a carbonyl under oligomerization conditions and mixtures thereof and a second component having the general formula (cyclopentadienyl)$_n$MY$_{4-n}$ where M is zirconium, hafnium and/or titanium, Y is individually selected from the group consisting of hydrogen, $C_1$–$C_5$ alkyl, $C_6$–$C_{20}$ aryl, $C_1$–$C_{25}$ metalloalkyl and halogen and n is an integer from 1 to 4. Preferably Y is hydrogen, methyl or chlorine. It is understood that when n is less than 3, the Ys may be the same or different. For the purposes of this invention, included within the definition of the above cyclopentadienyl moiety is the lower alkyl($C_1$–$C_5$)-substituted, preferably the methyl-substituted cyclopentadienyl moiety. Illustrative non-limiting examples of $C_1$–$C_{25}$ metalloalkyl groups are

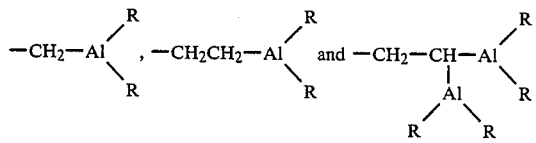

in which R is hydrogen, a $C_1$–$C_5$ alkyl group or a $C_1$–$C_5$ alkyl group or a $C_1$–$C_5$ metalloalkyl group.

The mole ratio of ruthenium carbonyl or compound to zirconium, hafnium and/or titanium will range from about 100:1 to about 1:100, more preferably from about 10:1 to about 1:10 and more preferably from about 2:01 to about 1:2. In a particularly preferred embodiment the mole ratio will be about 1:1.

Generally, carbon monoxide is added to the reaction mixture. While carbon monoxide is not absolutely needed when the carbonyls are used in the reaction mixture, its presence adds to the stability of the catalyst mixture. When ruthenium compounds are used, carbon monoxide is added to the reaction mixture to convert the ruthenium compounds to the carbonyls. The presence of hydrogen is not required in the reaction mixture. Its presence has no adverse effects and the use of syngas to provide the reaction mixture with carbon monoxide will also provide hydrogen.

The oligomerization is a liquid phase reaction. It is preferably carried out in the presence of a solvent, preferably an amine solvent. Most preferably the solvent is an aliphatic amine. Preferably the reactant amines are used as the reaction solvents. Other solvents such as alcohols, ethers, aromatics or paraffins can be used, but are less desirable.

The alkylation or oligomerization reaction conditions will vary considerably depending on the particular amine being alkylated. The higher molecular weight amines will require higher temperatures than the lower molecular weight amines. The optimum alkylation conditions can be determined by routine experimentation.

The oligomerization reaction is typically carried out at a temperature range of from about 50° C. to about 300° C., more preferably from about 150° C. to about 250° C., even more preferably from about 175° C. to about 250° C. Pressures will typically run from about 1 atmosphere to about 500 atmospheres, more preferably from about 1 to about 300 atmospheres and more preferably from about 20 to about 100 atmospheres.

The process of the instant invention may be accomplished in either a batch or continuous type operation. For example, when a batch type operation is to be employed, a quantity of the catalyst and amine compound along with an organic solvent, if one is to be used, will be placed in a pressure-resistant apparatus such as an autoclave of the stirring, mixing or rotating type. Following the addition of the catalyst and starting material, the apparatus is sealed, flushed with an inert gas such as nitrogen, and pressurized to the desired operating pressure with carbon monoxide and optionally hydrogen. Upon reaching the desired operating pressure, the apparatus is then heated to a predetermined operating temperature and maintained thereat for the desired residence time which may range from about 0.5 up to about 20 hours or more in duration. Upon completion of the desired residence time, heating is discontinued and after the apparatus and contents thereof have returned to room temperature, the excess pressure is discharged, the apparatus is opened, and the reaction mixture is recovered therefrom. After separation of the product mix from the catalyst, the former may then be subjected to conventional means of separating the components of said mix, said means including fractional distillation, fractional crystallization, etc.

It is also contemplated within the scope of this invention that the alkylation of the alkylamine compound may be accomplished in a continuous manner of operation. When such a type of operation is employed, the starting material comprising the alkylamine is continuously charged to an apparatus which is maintained at the proper operating conditions of temperature and pressure. In addition, the catalyst which is to be employed as well as any solvent is also continuously charged to the reaction apparatus either through separate lines or, if so desired, the components of the reaction mixture may be admixed prior to entry into the reaction apparatus and the resulting mixture charged thereto in a single stream. After passage through the apparatus for a predetermined period of time, the reactor effluent is continuously withdrawn and subjected to conventional means of separation whereby the product mix is separated from the catalyst and any unreacted starting material that is to be recycled to the reaction apparatus to form a portion of the feedstock, while the product mix is subjected to further distillation to recover the various components of said mix.

The process of this invention is further described by the following illustrative embodiments which are provided for illustration and are not to be construed as limiting the invention.

EXAMPLE 1

To a 100 cc stainless steel screw top autoclave was added 40 ml of triethylamine, 117 mg of triruthenium dodecacarbonyl($Ru_3(CO)_{12}$; 0.183 mmol) and 47.2 mg of bis(cyclopentadienyl)zirconium hydrogen chloride ($Cp_2ZrHCl$; 0.183 mmol). The autoclave was sealed under inert atmosphere and flushed with carbon monoxide, following which the autoclave was pressurized to 50 atmospheres with carbon monoxide. Thereafter, the autoclave was heated to a temperature of 220° C. and maintained there for a period of 19 hours. At the end of this period, heating was discontinued and the autoclave was allowed to return to room temperature. The excess pressure was discharged, the autoclave was opened, and the reaction product was recovered. The product was analyzed by means of gas liquid chromatography and mass spectroscopy. This analysis determined that there had been a 34% w conversion of the triethylamine and that the triethylamine which had been converted to higher alkylamines (50%) was converted with the selectivity shown in Table I below.

TABLE I

| Alkylated Product | Weight Percent |
|---|---|
| butyldiethylamine | 77.0 |
| hexyldiethylamine | 8.0 |
| ethyldibutylamine | 6.9 |

EXAMPLE 2

The above experiment was repeated using 48.2 grams of $CpZrCl_3$ (0.183 mmol) instead of 0.183 mmol of $Cp_2ZrHCl$. Analysis (after a 16 hr reaction time) determined that there had been a 74%w conversion of the triethylamine and that the triethylamine which had been converted to higher alkylamines (50%) was converted with the selectivity shown in Table II below.

TABLE II

| Alkylated Product | Weight Percent |
|---|---|
| butylethylamine | 22.2 |
| butyldiethylamine | 38.2 |
| hexyldiethylamine | 5.7 |
| ethyldibutylamine | 10.4 |
| octyldiethylamine | 3.1 |

EXAMPLE 3

The above experiment was repeated using 69.5 mg (0.183 mmol) of $Cp_2HfCl_2$ instead of 0.183 mmol of $CpZrCl_3$. Analysis (after a 16 hr reaction time) determined that there had been a 74% conversion of the triethylamine and that the triethylamine which had been converted to higher alkylamines (50%) was converted with the selectivity shown in Table III below.

TABLE III

| Alkylated Product | Weight Percent |
|---|---|
| butylethylamine | 21.8 |
| butyldiethylamine | 36.7 |
| hexyldiethylamine | 6.2 |
| dibutylethylamine | 9.7 |
| octyldiethylamine | 3.3 |

EXAMPLE 4

The above experiment was repeated using 40 ml of tributylamine (instead of triethylamine) and 45.6 mg (0.183 mmol) of $Cp_2TiCl_2$ instead of $Cp_2HfCL_2$. Analysis (after a 16.5 hr reaction time) determined that there had been a 43% conversion of the tributylamine and that the tributylamine which had been converted to higher alkylamines (50%) was converted to octyldibutylamine with a selectivity of 52.0%.

EXAMPLE 5

The above experiment was repeated using 40 ml of trihexylamine (instead of tributylamine) and 47.2 mg (0.183 mmol) of $Cp_2ZrHCl$ (instead of $Cp_2TiCl_2$). Analysis(after a 15 hr reaction time) determined that there had been a 14% conversion of the trihexylamine and that the trihexylamine which had been converted to higher alkylamines (50%) was converted to dodecyldihexylamine with a selectivity of 92% (with a 94% linearity).

COMPARATIVE EXAMPLE A

Example 1 above was repeated except that as catalyst only triruthenium dodecacarbonyl was used. Analysis (after an 18 hr reaction time) determined that there had only been a 2%w conversion of the triethylamine and that the triethylamine which had been converted to higher alkylamines (50%) was converted with the following selectivities: butyldiethylamine-92%w and hexyldiethylamine-7%w.

COMPARATIVE EXAMPLE B

Example 1 above was repeated except that as catalyst only $Cp_2ZrHCl$ was used. Analysis (after a 16 hr reaction time) determined that there had been a 2%w conversion of the triethylamine and that the triethylamine which had been converted to higher alkylamines (50%) was converted with a selectivity to butyldiethylamine of greater than 95%w.

I claim:

1. A process for the liquid phase oligomerization of alkylamines to produce longer carbon chain alkylamines which process comprises contacting said alkylamines at oligomerization reaction conditions with a catalyst mixture comprising a first component selected from a ruthenium carbonyl, a ruthenium-compound capable of being converted to a carbonyl under oligomerization conditions and mixtures thereof and a second compound having the general formula (cyclopentadienyl)$_n$MY$_{4-n}$ whrein M is zirconium, hafnium or titanium, Y is individually selected from the group consisting of hydrogen, $C_1$-$C_5$ alkyl, $C_6$-$C_{20}$ aryl, $C_1$-$C_{25}$ metalloalkyl and halogen, n is an integer from 1 to 4 and the mole ratio of ruthenium carbonyl or ruthenium-compound to (cyclopentadienyl)$_4$MY$_{4-n}$ ranges from about 10:1 to about 1:10.

2. The process of claim 1 wherein the ruthenium carbonyl is triruthenium dodecacarbonyl.

3. The process of claims 1 or 2 wherein the mole ratio ranges from about 2:1 to about 1:2.

4. The process of claim 1 wherein the alkylamine is a trialkylamine.

5. The process of claim 6 wherein the alkylamine is a $C_1$-$C_6$ trialkylamine.

6. The process of claim 5 wherein the trialkylamine is selected from triethylamine, tributylamine and trihexylamine.

7. The process of claim 1 wherein the longer carbon chain amine consists predominately of mono-alkylated amine.

8. The process of claim 1 wherein the temperature is maintained between about 50° C. and about 300° C.

9. The process of claim 8 wherein the temperature is between about 150° C. and about 250° C.

10. The process of claim 1 wherein the pressure is maintained between about 1 and about 500 atmospheres.

11. The process of claim 1 wherein Y is hydrogen, methyl and chlorine.

12. The process of claim 11 wherein Y is hydrogen and chlorine.

13. The process of claim 1 wherein n=1 or 2.

14. The process of claim 1 wherein carbon monoxide is additionally added.

15. A process for preparing an amine of the general formula

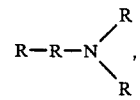

wherein R is $C_1$-$C_6$ alkyl, which process comprises oligomerizing an amine of the general formula

wherein R is as defined above by contacting in the liquid phase said

at a temperature of from about 175° C. to about 250° C. with a catalyst mixture comprising a first component selected from a ruthenium carbonyl, a ruthenium-compound capable of being converted to a carbonyl under oligomerization conditions and mixtures thereof and a second component having the general formula (cyclopentadienyl)$_n$MY$_{4-n}$ wherein M is selected from zirconium, hafnium and titanium, Y is individually selected from hydrogen, methyl and chlorine and n is 1 or 2 and wherein the molar ratio of ruthenium carbonyl or ruthenium compound to (cyclopentadienyl)$_n$MY$_{4-n}$ ranges from about 2:1 to about 1:2.

16. The process of claim 15 wherein carbon monoxide is additionally added.

17. The process of claims 15 or 16 wherein R is selected from $C_2$, $C_4$ and $C_6$.

* * * * *